US010772822B2

(12) United States Patent
Greaves et al.

(10) Patent No.: US 10,772,822 B2
(45) Date of Patent: Sep. 15, 2020

(54) MOLECULARLY IMPRINTED POLYMERS AND THEIR USE AS ANTIDANDRUFF AGENTS

(71) Applicant: L'ORÉAL, Paris (FR)

(72) Inventors: Andrew Greaves, Magny-le-hongre (FR); Christèle Ribaud, Nogent S/Marne (FR); Franco Manfre, Le Perreux sur Marne (FR); Karsten Haupt, Compiègne (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/655,381

(22) PCT Filed: Dec. 20, 2013

(86) PCT No.: PCT/EP2013/077787
§ 371 (c)(1),
(2) Date: Jun. 25, 2015

(87) PCT Pub. No.: WO2014/102206
PCT Pub. Date: Jul. 3, 2014

(65) Prior Publication Data
US 2015/0342859 A1  Dec. 3, 2015

Related U.S. Application Data (60) Provisional application No. 61/773,178, filed on Mar. 6, 2013.

(30) Foreign Application Priority Data

Dec. 26, 2012 (FR) .................................... 12 62782

(51) Int. Cl.
*A61K 8/81* (2006.01)
*C08J 9/28* (2006.01)
(Continued)

(52) U.S. Cl.
CPC .............. *A61K 8/8158* (2013.01); *A61K 8/81* (2013.01); *A61K 8/817* (2013.01); *A61K 8/8152* (2013.01);
(Continued)

(58) Field of Classification Search
CPC .... B01J 20/268; A61K 8/8158; A61K 8/8152; A61Q 5/006
See application file for complete search history.

(56) References Cited

U.S. PATENT DOCUMENTS 3,792,068 A    2/1974  Luedders et al.
5,630,978 A *  5/1997  Domb .................... B01J 20/268
                                                        264/330
(Continued)

FOREIGN PATENT DOCUMENTS

EP    0925776 A2    6/1999
EP    0972512 A1    1/2000
(Continued)

OTHER PUBLICATIONS

Silvana Obici, Zhaohui Feng, Kimyata Morgan, Daniel Stein, George Karkanias, and Luciano Rossetti. Central Administration of Oleic Acid Inhibits Glucose Production and Food Intake. Diabetes, 2002, pp. 271-275.*
(Continued)

*Primary Examiner* — Michael M Dollinger
*Assistant Examiner* — Christina H. W. Rosebach
(74) *Attorney, Agent, or Firm* — The Marbury Law Group, PLLC (57) ABSTRACT

The invention relates to a molecularly imprinted polymer obtained by polymerization of a mixture comprising a basic ethylene monomer having an amine group, a crosslinking agent comprising at least 2 polymerizable ethylene unsaturations, a porogenic solvent and a $C_{14}$-$C_{20}$ fatty acid. A
(Continued)

cosmetic composition comprising such a polymer. A cosmetic process to prevent and/or treat dandruff of the scalp using such a polymer.

16 Claims, 1 Drawing Sheet

(51) Int. Cl.
*A61Q 5/00* (2006.01)
*C08F 20/34* (2006.01)
*C08F 20/60* (2006.01)
*C08F 26/08* (2006.01)
*C08F 2/04* (2006.01)

(52) U.S. Cl.
CPC ............... *A61Q 5/00* (2013.01); *A61Q 5/006* (2013.01); *C08F 2/04* (2013.01); *C08F 20/34* (2013.01); *C08F 20/60* (2013.01); *C08F 26/08* (2013.01); *C08J 9/28* (2013.01); *A61K 2800/54* (2013.01)

(56) References Cited

U.S. PATENT DOCUMENTS

| | | | |
|---|---|---|---|
| 5,932,199 | A | 8/1999 | Esser |
| 6,057,377 | A | 5/2000 | Sasaki et al. |
| 6,255,421 | B1 * | 7/2001 | Plochocka ............... A61K 8/06 526/194 |
| 6,649,212 | B2 | 11/2003 | Payne et al. |
| 6,916,465 | B2 | 7/2005 | Panzer et al. |
| 7,820,770 | B2 | 10/2010 | Schoeley et al. |
| 8,114,921 | B2 | 2/2012 | Poulton et al. |
| 8,679,859 | B2 | 3/2014 | Yan et al. |
| 9,956,542 | B2 | 5/2018 | Haupt et al. |
| 10,335,355 | B2 | 7/2019 | Greaves |
| 2003/0020049 | A1 | 1/2003 | Payne et al. |
| 2005/0063928 | A1 | 3/2005 | Witham et al. |
| 2005/0084464 | A1 | 4/2005 | McGrath et al. |
| 2005/0084474 | A1 | 4/2005 | Wu et al. |
| 2009/0148961 | A1 * | 6/2009 | Luchini ............... B01J 20/28095 436/518 |
| 2009/0291058 | A1 | 11/2009 | Woodland et al. |
| 2010/0048737 | A1 * | 2/2010 | Wendel ................ A61K 8/8117 514/772.5 |
| 2010/0254932 | A1 | 10/2010 | Benabdillah et al. |
| 2012/0100358 | A1 | 4/2012 | Haupt et al. |
| 2013/0085186 | A1 | 4/2013 | Wendel et al. |
| 2014/0076346 | A1 | 3/2014 | Bourdin et al. |
| 2014/0205556 | A1 | 7/2014 | Bourdin et al. |
| 2016/0143832 | A1 | 5/2016 | Greaves |

FOREIGN PATENT DOCUMENTS

| | | |
|---|---|---|
| EP | 1146057 A1 | 10/2001 |
| EP | 1658863 A1 | 5/2006 |
| JP | 2000-086446 A | 3/2000 |
| WO | 2006/062926 A1 | 6/2006 |
| WO | 2008/034764 A2 | 3/2008 |
| WO | 2014/102077 A1 | 7/2014 |
| WO | 2014/102078 A1 | 7/2014 |
| WO | 2014/102209 A1 | 7/2014 |

OTHER PUBLICATIONS

Non-Final Office Action for co-pending U.S. Appl. No. 14/655,395 (dated Jun. 17, 2016).
International Search Report for PCT/EP2013/077787, dated Feb. 17, 2014.
International Search Report for PCT/EP2013/076659, dated Apr. 10, 2014.
International Search Report for PCT/EP2013/076655, dated Mar. 18, 2014.
International Search Report for PCT/EP2013/077790, dated Apr. 11, 2014.
First Office Action for counterpart Chinese Application No. 201380068610.6, dated Mar. 4, 2016. (English translation).
Second Office Action for counterpart Chinese Application No. 201380068610.6, dated Oct. 8, 2016. (English translation).
Sangeetha, Neralagatta M. et al., "Supramolecular gels: Functions and uses," Chemical Society Reviews, published Aug. 2005, pp. 821-836.
Final Office Action for copending U.S. Appl. No. 14/655,395, dated Feb. 9, 2017.
Final Office Action for copending U.S. Appl. No. 14/655,386, dated May 4, 2018.
Non-Final Office Action for copending U.S. Appl. No. 14/655,390, dated Aug. 28, 2018.
Final Office Action for copending U.S. Appl. No. 14/655,395, dated Sep. 4, 2018.
Vasapollo, G., et al., "Molecularly Imprinted Polymers: Present and Future Prospective," International Journal of Molecular Sciences, 2001, 12, pp. 5908-5945.
Mayes et al., "Molecularly imprinted polymers: useful materials for analytical chemistry?," trends in analytical chemistry, vol. 16, No. 6, 1997, pp. 321-332.
Mujahid et al., "Chemical Sensors Based on Molecularly Imprinted Sol-Gel Materials," Materials 2010, 3, pp. 2196-2217.
Non-Final Office Action for copending U.S. Appl. No. 14/655,390, dated May 3, 2017.
Non-Final Office Action for copending U.S. Appl. No. 14/655,386, dated Sep. 6, 2017.
Final Office Action for copending U.S. Appl. No. 14/655,390, dated Jan. 25, 2018.
Non-Final Office Action for copending U.S. Appl. No. 14/655,395, dated Nov. 2, 2017.
Co-pending U.S. Appl. No. 16/208,709, filed Dec. 4, 2018.
Non-Final Office Action for copending U.S. Appl. No. 14/655,386, dated Nov. 1, 2018.
Final Office Action for co-pending U.S. Appl. No. 14/655,390, dated May 8, 2019.
Non-Final Office Action for co-pending U.S. Appl. No. 14/655,386, dated Jan. 22, 2020.
Non-Final Office Action for co-pending U.S. Appl. No. 16/208,709, dated Sep. 18, 2019.
Final Office Action for copending U.S. Appl. No. 16/208,709, dated Jun. 5, 2020.

* cited by examiner

MOLECULARLY IMPRINTED POLYMERS AND THEIR USE AS ANTIDANDRUFF AGENTS

CROSS REFERENCE TO RELATED APPLICATIONS

This is a national stage application of PCT/EP2013/077787, filed internationally on Dec. 20, 2013, which claims priority to U.S. Provisional Application No. 61/773,178, filed on Mar. 6, 2013; as well as French Application 1262782, filed on Dec. 26, 2012, all of which are incorporated herein by reference in their entireties.

The invention relates to specific molecularly imprinted polymers, and a cosmetic composition containing them, and their use to remove or reduce dandruff of the scalp.

The appearance of dandruff, a desquamation problem of the scalp, is bothersome both aesthetically and because of the trouble it causes (itching, redness, etc.), so that many people confronted with this problem to variable degrees wish to eliminate it efficiently and permanently.

Dandruff corresponds to excessive and visible desquamation of the scalp resulting from excessively rapid multiplication of the epidermal cells. This phenomenon may be caused in particular by microtraumas of physical or chemical nature, such as excessively aggressive hair treatments, extreme climatic conditions, nervousness, diet, fatigue and pollution, but it has been demonstrated that dandruff conditions usually result from a disorder of the microflora of the scalp and are more particularly due to the excessive colonization of a yeast belonging to the family of yeasts of the *Malassezia* genus (previously known as *Pityrosporum ovale*) and which is naturally present on the scalp.

To combat dandruff, using anti-fungal agents applied topically is known. Because of their anti-fungal power these agents attempt to remove or control the multiplication of a yeast that is present in the scalp, belonging to the genus *Malassezia* and its variants (*M. ovalis, M. orbiculare, M. furfur, M. globosa*, etc.). As antidandruff agents used for their antifungal action, zinc pyrithione, piroctone olamine, selenium disulfide can be cited. These active agents may have an unfavourable impact on the overall quality of the scalp, including scalp dryness, hair colour and the environment (*The Antiseptic* 2004; 201(1), 5-8).

In the article "Three Etiologic Facets of Dandruff and Seborrheic Dermatitis: *Malassezia* Fungi, Sebaceous Lipids, and Individual Sensitivity" Y. M. DeAngelis et al, J. Investig. Dermatol Symp Proc 10:295-297, 2005, it is stated that the oleic acid present in sebum causes the production of *Malassezia*, causing dandruff to form.

Therefore a need remains to find new antidandruff agents that are effective without the drawbacks raised hereinabove, particularly that have no antifungal activity and could neutralize the action of oleic acid on the scalp and thereby prevent the excessive colonization of the scalp by *Malassezia* sp.

The Applicant has now found in a surprising manner that the use of certain imprinted polymers as defined hereinafter can specifically trap the $C_{14}$-$C_{20}$ fatty acids that cause dandruff to form, particularly oleic acid.

Accordingly, these specific molecularly imprinted polymers can trap the oleic acid present on the scalp thereby preventing the colonization of the scalp by *Malassezia*. Therefore they reduce or prevent dandruff appearing.

The present invention therefore relates to a molecularly imprinted polymer that can be obtained according to a process comprising a first step of polymerization of a mixture comprising:
  i) one or more basic ethylene monomer(s) as defined hereinafter;
  ii) one or more crosslinking agent(s) comprising at least 2 polymerizable ethylene unsaturations;
  iii) one or more porogenic solvent(s);
  iv) one or more $C_{14}$-$C_{20}$ fatty acid(s),
followed by a second step of removing the $C_{14}$-$C_{20}$ fatty acid present in the polymer obtained from the first step.

The invention further relates to a process for preparing molecularly imprinted polymers as defined hereinafter.

DETAILED DESCRIPTION

The invention further relates to a cosmetic composition comprising, in a physiologically acceptable medium, a molecularly imprinted polymer as defined previously.

A further object of the invention is a cosmetic process to prevent and/or treat dandruff of the scalp, in particular that caused by yeasts from the genus *Malassezia*, characterized in that it comprises the application of an imprinted polymer, as defined previously, or a cosmetic composition comprising it, to the scalp.

A further object of the invention is the cosmetic use of an imprinted polymer as defined previously as an active agent to prevent and/or treat dandruff of the scalp.

Molecularly Imprinted Polymers or MIPs are materials that are widely used for their applications in the fields of biotechnology, chemistry, chromatography, analytical chemistry, and biology (*J. Mol. Recognit.*, 19, 106-180 (2006); *Molecularly Imprinted Materials: Science and Technology*, Marcel Dekker, NY, M. Yan and O. Ramstrom (2005)). The concept of molecular imprint relates to Emil Fisher's famous lock and key fit principle known since 1894 for enzymes and their ligand (*Advances in Carbohydrate Chemistry and Biochemistry*, 1-20 (1994)). Molecular imprint consists more specifically in making a polymer comprising cavities with specific shape and size of a targeted molecule or "imprint", also called "template" that uses a template for the formation of recognition sites having complementary shape for the imprinted molecule. The molecular imprints are polymers prepared from functional monomers that are polymerized around a molecule, also called a template. The monomer is therefore chosen so as to develop non-covalent interactions (hydrogen and electrostatic bonds, ionic and non-ionic interactions or even low energy interactions such as Van der Waals bonds, or π-π stacking) with the template. The polymerization then occurs between the monomers complexed with the template and a crosslinking agent in a solvent called a "porogenic solvent" so as to form specific cavities. The bonds between the template and the polymerized monomers are then broken using suitable solvents to extract the template from the polymeric support. Template molecule extraction then leaves vacant recognition sites with high affinity for the target molecule. The shape and size of the imprint and the spatial arrangement of the functional groups inside of the recognition cavity are complementary to the template molecule and contain interaction sites that are specific to this same molecule.

This type of selective trapping is described in several scientific articles (See for example *Analytical Chemistry* "Molecularly imprinted polymers: the next generation", 75(17), 376-383, (2003); *Chemical Engineering Journal*, "Selective separation of basic and reactive dyes by molecularly imprinted polymers (MIPs)", 149(1-3), 263-272, (2009), *Kirk-Othmer Encyclopedia of Chemical Technology* "Molecular Imprinting" D. Spivak; accessible online since 25 Jun. 2010, DOI: 10.1002/0471238961.molespiv.a01; *Molecularly Imprinted Polymers*; B. R. Hart, K. J. Shea, http://onlinelibrary.wiley.com/doi/10.1002/0471216275.esm054/full, *Encyclopedia of Polymer, Science and Technology*, accessible online since 15 Jul. 2002; DOI: 10.1002/0471216275.esm054; J. Sep. Sci, M. Lasàkovà, P. Jandera, 32, 799-812).

The molecularly imprinted polymer according to the invention can be obtained according to a process comprising a first polymerization step of a mixture comprising:
  i) one or more basic ethylene monomers as defined hereinafter;
  ii) one or more crosslinking agents comprising at least 2 polymerizable ethylene unsaturations;
  iii) one or more porogenic solvents; in the presence of
  iv) one or more $C_{14}$-$C_{20}$ fatty acids,
followed by a second step of removing the $C_{14}$-$C_{20}$ fatty acid present in the polymer obtained from the first step.

The basic ethylene monomer used in the polymerization step is an ethylene monomer comprising an amine group, i.e. a group chosen from primary amine, secondary amine, tertiary amine and quaternary ammonium. An amide group is not considered as being an amine group.

As basic ethylene monomer comprising an amine group, the following can be cited:
  (meth)acrylates and (meth)acrylamides having an amine group having formula (I):

(I)

in which $R_1$ denotes H or methyl, X denotes O or NH, R denotes a divalent $C_1$-$C_4$ alkylene group,
Z denotes an —$NR_2R_3$ or —$N^+R_2R_3R_4$ group, $X^-$ $R_2$, $R_3$ and $R_4$ denoting independently of each other H or a $C_1$-$C_4$ alkyl,
$X^-$ being an anion chosen from halides (chloride, bromide or iodide) or ($C_2$-$C_6$)alkyl sulfates more particularly methylsulfate, phosphates, ($C_2$-$C_6$)alkyl- or ($C_2$-$C_6$)alkyl($C_6$-$C_{10}$) aryl sulfonates, anions derived from an organic acid such as acetate or lactate;
  N-(meth)acryloyl-p-aminobenzamidine having formula (II):

(II)

in which $R'_1$ denotes H or methyl, and $R'_2$, $R'_3$, $R'_4$ denote, independently of each other, H or a $C_1$-$C_4$ alkyl group;
  styryl amidines having formula (III):

(III)

in which $R_5$, $R_6$, $R_7$ denote, independently of each other, H or a $C_1$-$C_4$ alkyl group;
  amino styrenes having formula (IV):

(IV)

in which Z' denotes a —$NR_8R_9$ or —$N^+R_8R_9R_{10}X^-$ group $R_8$, $R_9$ and $R_{10}$ denote, independently of each other, H or a $C_1$-$C_4$ alkyl;
$X^-$ being an anion chosen from halides (chloride, bromide or iodide) or ($C_2$-$C_6$)alkyl sulfates more particularly methylsulfate, phosphates, ($C_2$-$C_6$)alkyl- or ($C_2$-$C_6$)alkyl ($C_6$-$C_{10}$) arylsulfonates, anions derived from an organic acid such as acetate or lactate;
W denotes a R" or OR" group, R" being a $C_1$-$C_4$ alkyl group;
n being an integer equal to 0, 1 or 2;
  vinylpyridines having formula (V):

in which Y denotes a R'" or OR'" group, R'" being a $C_1$-$C_4$ alkyl group;
mn being an integer equal to 0, 1 or 2.

As monomer (I) the following can be cited: 2-aminoethyl methacrylate, 2-aminoethyl acrylate, 3-aminopropyl methacrylate, 3-aminopropyl acrylate, 4-aminobutyl methacrylate, 4-aminobutyl acrylate, N-methyl-2-aminoethyl methacrylate, N-methyl-2-aminoethyl acrylate, N-methyl-3-aminopropyl methacrylate, N-methyl-3-aminopropyl acrylate, N-methyl-4-aminobutyl methacrylate, N-methyl-4-aminobutyl acrylate, N-ethyl-2-aminoethyl methacrylate, N-ethyl-2-aminoethyl acrylate, N-ethyl-3-aminopropyl methacrylate, N-ethyl-3-aminopropyl acrylate, N-ethyl-4-aminobutyl methacrylate, N-ethyl-4-aminobutyl acrylate, N,N-dimethyl-2-aminoethyl methacrylate, N,N-dimethyl-2-aminoethyl acrylate, N,N-dimethyl-3-aminopropyl methacrylate, N,N-dimethyl-3-aminopropyl acrylate, N,N-dimethyl-4-aminobutyl methacrylate, N,N-dimethyl-4-aminobutyl acrylate, N,N-diethyl-2-aminoethyl methacrylate, N,N-diethyl-2-aminoethyl acrylate, N,N-diethyl-3-aminopropyl methacrylate, N,N-diethyl-3-aminopropyl acrylate, N,N-diethyl-4-aminobutyl methacrylate, N,N-diethyl-4-aminobutyl acrylate, N,N,N-trimethyl-2-ammonium ethyl methacrylate chloride (having formula CH$_2$=C(CH$_3$)—C(O)O—(CH$_2$)$_2$N$^+$(CH$_3$)$_3$Cl—), ethyl N,N,N-trimethyl-2-ammonium acrylate chloride, N,N,N-trimethyl-3-ammonium propyl methacrylate chloride, N,N,N-trimethyl-3-ammonium propyl acrylate chloride, N,N,N-trimethyl-4-ammonium butyl methacrylate chloride, N,N,N-trimethyl-4-ammonium butyl acrylate chloride, N,N,N-triethyl-2-ammonium ethyl methacrylate chloride (having formula CH$_2$=C(CH$_3$)—C(O)O—(CH$_2$)$_2$N$^+$(CH$_2$CH$_3$)$_3$Cl—), ethyl N,N,N-triethyl-2-ammonium acrylate chloride, N,N,N-triethyl-3-ammonium propyl methacrylate chloride, N,N,N-triethyl-3-ammonium propyl acrylate chloride, N,N,N-triethyl-4-ammonium butyl methacrylate chloride, N,N,N-triethyl-4-ammonium butyl acrylate chloride, 2-aminoethyl methacrylamide, 2-aminoethyl acrylamide, 3-aminopropyl methacrylamide, 3-aminopropyl acrylamide, 4-aminobutyl methacrylamide, 4-aminobutyl acrylamide, N-methyl-2-aminoethyl methacrylamide, N-methyl-2-aminoethyl acrylamide, N-methyl-3-aminopropyl methacrylamide, N-methyl-3-aminopropyl acrylamide, N-methyl-4-aminobutyl methacrylamide, N-methyl-4-aminobutyl acrylamide, N-ethyl-2-aminoethyl methacrylamide, N-ethyl-2-aminoethyl acrylamide, N-ethyl-3-aminopropyl methacrylamide, N-ethyl-3-aminopropyl acrylamide, N-ethyl-4-aminobutyl methacrylamide, N-ethyl-4-aminobutyl acrylamide, N,N-dimethyl-2-aminoethyl methacrylamide, N,N-dimethyl-2-aminoethyl acrylamide, N,N-dimethyl-3-aminopropyl methacrylamide, N,N-dimethyl-3-aminopropyl acrylamide, N,N-dimethyl-4-aminobutyl methacrylamide, N,N-dimethyl-4-aminobutyl acrylamide, N,N-diethyl-2-aminoethyl methacrylamide, N,N-diethyl-2-aminoethyl acrylamide, N,N-diethyl-3-aminopropyl methacrylamide, N,N-diethyl-3-aminopropyl acrylamide, N,N-diethyl-4-aminobutyl methacrylamide, N,N-diethyl-4-aminobutyl acrylamide, N,N,N-trimethyl-2-ammonium ethyl methacrylamide chloride (having formula CH$_2$=C(CH$_3$)—C(O)O—(CH$_2$)$_2$N$^+$(CH$_3$)$_3$Cl—), ethyl N,N,N-trimethyl-2-ammonium acrylamide chloride, N,N,N-trimethyl-2-ammonium ethyl methacrylamide methylsulfate, N,N,N-trimethyl-2-ammonium ethyl acrylamide methylsulfate, N,N,N-trimethyl-3-ammonium propyl methacrylamide chloride, N,N,N-trimethyl-3-ammonium propyl acrylamide chloride, N,N,N-trimethyl-4-ammonium butyl methacrylamide chloride, N,N,N-trimethyl-4-ammonium butyl acrylamide chloride, N,N,N-trimethyl-3-ammonium propyl methacrylamide methylsulfate, N,N,N-trimethyl-3-ammonium propyl acrylamide methylsulfate, N,N,N-trimethyl-4-ammonium butyl methacrylamide methylsulfate, N,N,N-trimethyl-4-ammonium butyl acrylamide methylsulfate, N,N,N-triethyl-2-ammonium ethyl methacrylamide chloride (having formula CH$_2$=C(CH$_3$)—C(O)O—(CH$_2$)$_2$N$^+$(CH$_2$CH$_3$)$_3$Cl—), ethyl N,N,N-triethyl-2-ammonium acrylamide chloride, N,N,N-triethyl-3-ammonium propyl methacrylamide chloride, N,N,N-triethyl-3-ammonium propyl acrylamide chloride, N,N,N-triethyl-4-ammonium butyl methacrylamide chloride, N,N,N-triethyl-4-ammonium butyl acrylamide chloride, N,N,N-triethyl-2-ammonium ethyl methacrylamide ethylsulfate (having formula CH$_2$=C(CH$_3$)—C(O)O—(CH$_2$)$_2$N$^+$(CH$_2$CH$_3$)$_3$Cl—), ethyl N,N,N-triethyl-2-ammonium acrylamide ethylsulfate, N,N,N-triethyl-3-ammonium propyl methacrylamide ethylsulfate, N,N,N-triethyl-3-ammonium propyl acrylamide ethylsulfate, N,N,N-triethyl-4-ammonium butyl methacrylamide ethylsulfate, N,N,N-triethyl-4-ammonium butyl acrylamide ethylsulfate.

As monomer (II), the following can be cited: N-acryloyl-p-aminobenzamidine, N-methacryloyl-p-aminobenzamidine, N-acryloyl-N-methyl-p-aminobenzamidine, N-methacryloyl-N-methyl-p-aminobenzamidine, N-acryloyl-N-ethyl-p-aminobenzamidine, N-methacryloyl-N-ethyl-p-aminobenzamidine, N-acryloyl-N-propyl-p-aminobenzamidine, N-methacryloyl-N-propyl-p-aminobenzamidine, N-acryloyl-N-butyl-p-aminobenzamidine, N-methacryloyl-N-butyl-p-aminobenzamidine, N-acryloyl-N,N-diethyl-p-aminobenzamidine, N-methacryloyl-N,N-diethyl-p-aminobenzamidine.

N-acryloyl-p-aminobenzamidine is preferred.

As monomer (III), 4-styrylamidine, N-ethyl-4-styrylamidine, N-propyl-4-styrylamidine, N-butyl-4-styrylamidine, N,N'-diethyl-4-styrylamidine, N,N'-dipropyl-4-styrylamidine, N,N'-butyl-4-styrylamidine can be cited. 4-styrylamidine is preferred.

As monomer (IV), para-amino styrene, para-N-methylamino styrene, para-N-ethylamino styrene, para-N-propylamino styrene, para-N-butylamino styrene, para-N,N-diethylamino styrene can be cited. para-amino styrene is preferred.

As monomer (V), 2-vinylpyridine, 3-vinylpyridine, 4-vinylpyridine can be cited. 4-Vinylpyridine is preferred.

Preferably, an ethylene monomer having formula (I) or formula (II) is used.

Preferably, N-acryloyl-p-aminobenzamidine is used.

Preferably, 2-aminoethyl methacrylate is used.

The mixture comprising the basic ethylene monomer with an amine group may comprise one or more additional neutral ethylene monomers, i.e. a monomer not containing an acid group (such as carboxylic acid, sulfonic acid) or a primary amine, secondary amine, tertiary amine or quaternary ammonium group.

The neutral additional monomer may be chosen from (meth)acrylamide, C$_1$-C$_6$ alkyl (meth)acrylates, C$_1$-C$_6$ hydroxyalkyl (meth)acrylates, acrylonitrile, styrene, (C$_1$-C$_4$) alkyl stryrenes, 1-allyl-(thio)urea, vinylpyrrolidone.

The polymerization is conducted in the presence of a crosslinking agent comprising at least 2 polymerizable ethylene unsaturations.

More specifically, the crosslinking agent is chosen from monomers having the following formula (C3) or (C4):

in which:

A is a phenyl optionally substituted by —COOH;

$R^8$, the same or different, represents a hydrogen atom or a linear or branched ($C_1$-$C_8$)alkyl group, preferably $C_1$-$C_6$ such as methyl;

$X^1$ and $X^2$, the same or different, are as defined previously; preferably $X^1$=O or NH, and $X^2$=O; and more particularly $X^1$=$X^2$=an oxygen atom, or else $X^1$ forms a bond;

W represents: i) either a 5- or 6-membered heteroaryl group such as pyridinyl or a 5- to 8-membered heterocycloalkyl group comprising at least one oxygen atom such as tetrahydrofuryl, piperazynyl or hexahydrofuro[3,2-b]furanyl, ii) or a *-A-($CR^9R^{10}$)$_x$-A* group when w is 2, with A as defined previously, $R^9$ and $R^{10}$, the same or different, representing a hydrogen atom or a ($C_1$-$C_6$)alkyl group such as methyl, x represents an integer comprised between 0 and 10 inclusive, preferably x=1 and * represents the attachment point to the —$X^1$—C($X^2$)—C(=$CH_2$)—$R^8$ groups; iii) or a linear or branched polyvalent hydrocarbon-based chain, preferably di or trivalent, saturated or unsaturated, preferably saturated, comprising from 1 to 20 carbon atoms optionally substituted by a hydroxyl group or by a phenyl group;

n represents an integer comprised between 0 and 5 inclusive; more particularly between 0 and 3, such as n=0 or 1;

u and w represent an integer comprised between 2 and 10 inclusive, more particularly between 2 and 5, such as u=2 and w=2 or 3.

Preferably W represents a $C_1$-$C_6$ divalent or a $C_1$-$C_{10}$ trivalent alkyl group.

According to a preferred variant of the invention, the monomers having formula (C3) and (C4) are chosen from the compounds in the following table:

| Name | Abbreviation | Structure |
| --- | --- | --- |
| Styrene/divinyl benzene | (DVB) | |
| Diisopropyl benzene | (DIB) | |
| 1,3-phenylene diacrylamide; 1,4-phenylene diacrylamide | | |
| N,N'-1,3-phenylenebis(2-methyl-2-propenamide); N,N'-1,4-phenylenebis(2-methyl-2-propenamide) | | |
| 3,5-bisacrylamido-benzoic acid where R" are identical and equal to H; and 3,5-bismethylacrylamido-benzoic acid where R" are identical and equal to $CH_3$ | | R" = H or $CH_3$ |
| 2,6-bisacryloylamidopyridine where R" are identical and equal to H; 2,6-bismethylacryloylamidopyridine where R" are identical and equal to $CH_3$ | | R" = H or $CH_3$ |

-continued

| Name | Abbreviation | Structure |
|---|---|---|
| 1,4-diacryloylpiperazine where R″ are identical and equal to H; 1,4-dimethylacryloylpiperazine where R″ are identical and equal to CH₃ | (DAP) | <br>R″ = H or CH₃ |
| Ethylene glycol dimethacrylate where R″ are identical and equal to CH₃ (EGDMA); Diacrylate ethylene glycol where R″ are identical and equal to H | (EGDMA) | <br>R″ = H or CH₃ |
| Tetramethylene dimethacrylate where R″ are identical and equal to CH₃; Tetramethylene diacrylate where R″ are identical and equal to H | (TDMA) | <br>R″ = H or CH₃ |
| Hexamethylene dimethacrylate where R″ are identical and equal to CH₃ and Hexamethylene diacrylate where R″ are identical and equal to H | | <br>R″ = H or CH₃ |
| Anhydroerythritoldimethacrylate where R″ are identical and equal to CH₃ and Anhydroerythritoldiacrylate where R″ are identical and equal to H | | <br>R″ = H or CH₃ |
| 1,4;3,6-dianhydro-p-sorbitol-2,5-dimethacrylate where R″ are identical and equal to CH₃; 1,4;3,6-dianhydro-p-sorbitol-2,5-diacrylate where R″ are identical and equal to H | | <br>R″ = H or CH₃ |
| Isopropylenebis(1,4-phenylene)-dimethacrylate where R″ are identical and equal to CH₃; Isopropylenebis(1,4-phenylene)-diacrylate R″ are identical and equal to H | | <br>R″ = H or CH₃ |

-continued

| Name | Abbreviation | Structure |
|---|---|---|
| 2,2-bis(Hydroxymethyl)butanol trimethacrylate where R″ are identical and equal to CH₃ (TRIM); 2,2-bis(Hydroxymethyl)butanol triacrylate R″ are identical and equal to H | (TRIM) | R″ = H or CH₃ |
| Pentaerythritol triacrylate where R″ are identical and equal to H; Pentaerythritol trimethacrylate where R″ are identical and equal to CH₃ | | R″ = H or CH₃ |
| Pentaerythritol tetraacrylate where R″ are identical and equal to H (PETRA); Pentaerythritol tetramethacrylate where R″ are identical and equal to CH₃ | (PETRA) | R″ = H or CH₃ |
| N,O-bismethacryloyl-ethanolamine where $R_c$ is equal to ethylene and R″ are identical and equal to CH₃ | (NOBE) | $R_c$ = (C₁-C₆)alkylene such as ethylene<br>R″ = H or CH₃ |
| N,N'-methylene-bis-acrylamide where $R_c$ = CH₂ (MDAA); or N,N-1,2-ethanediylbis(2-methyl-2-propenamide) N,N'-ethylene-bis-acrylamide where $R_c$ =CH₂—CH₂; N,N'-butylene-bis-acrylamide where $R_c$ = CH₂—CH₂—CH₂—CH₂; N,N'-hexylene-bis-acrylamide where $R_c$ = CH₂—CH₂—CH₂—CH₂—CH₂—CH₂ | (MDAA) | $R_c$ = (C₁-C₆)alkylene<br>R″ = H or CH₃ |

The crosslinking agent is preferably hexamethylene dimethacrylate (or 1,6-hexanediol dimethacrylate).

According to a specific embodiment of the invention the mass quantity of crosslinking agent in the pre-polymerization mixture (first step) is found in excess compared to the mass quantity of the basic ethylene monomer having an amine group and additional ethylene monomers if present. Preferably, the quantity of crosslinking agent, as a mass percentage, is greater than or equal to 50%. More preferably is greater than or equal to 80%.

Particularly the ratio of the number of moles of basic ethylene monomers having an amine group and additional ethylene monomers if present on the number of moles of crosslinking agents is less than or equal to 1/3 (mole/mole), more particularly the ratio is less than or equal to 1/5.

According to an advantageous embodiment of the invention the quantities of $C_{14}$-$C_{20}$ fatty acid imprint molecule (T), of basic ethylene monomer having an amine group and additional ethylene monomer if present (M) and of crosslinking agent (CL) added to the pre-polymerization mixture are found in a T/M/CL molar ratio comprised between 1:0.4:8 and 1:8:40 inclusive.

The Porogenic Solvent

The molecularly imprinted polymers are prepared from a porogenic solvent that preferably has polarity that i) can solubilize the $C_{14}$-$C_{20}$ fatty acid imprint molecule and/or ii) is suited for said $C_{14}$-$C_{20}$ fatty acid imprint molecule interacting with the molecularly imprinted polymer. "Porogenic solvent" is understood to mean a solvent that can create a porous network capable of feeding the $C_{14}$-$C_{20}$ fatty acid molecules to the imprints in the polymer.

The porogenic solvent must also favour the $C_{14}$-$C_{20}$ fatty acid imprint molecule-monomer interactions and the stability of the complex formed.

According to a preferred embodiment, when the solubilization of the imprint molecule in the pre-polymerization mixture requires it, the porogenic solvent is chosen from the polar protic organic solvents such as water, $C_1$-$C_8$ alcohols such as ethanol.

According to another preferred embodiment the porogenic solvent is a non-protic polar solvent such as acetonitrile, tetrahydrofuran (THF), dialkylformamide (dimethylformamide, diethylformamide), N-methyl-2-pyrrolidinone (NMP), N-ethyl-2-pyrrolidinone (NEP), N,N'-dimethylpropylene-urea (DMPU), and dimethylsulfoxide (DMSO).

A mixture of porogenic solvents can be used.

Preferably the porogenic solvent used according to the invention is a solvent chosen from polar protic or aprotic solvents such as water, $C_1$-$C_8$ alcohols such as ethanol, and acetonitrile, and mixtures thereof.

The Imprint or Template Molecules:

The aim of the invention is to make available a molecularly imprinted polymer that captures the saturated or unsaturated $C_{14}$-$C_{20}$ carboxylic fatty acids, particularly oleic acid, on the surface of the scalp.

As seen previously, the $C_{14}$-$C_{20}$ carboxylic fatty acid "template" is a compound that mimics oleic acid, which causes dandruff within the molecularly imprinted polymer, so that the molecularly imprinted polymer can then capture oleic acid when it is applied to the scalp.

As saturated or unsaturated $C_{14}$-$C_{20}$ carboxylic fatty acid, the following can be cited: myristic acid (C14:0), myristoleic acid (C14:1), pentadecanoic acid (C15:0), palmitic acid (C16:0), palmitoleic acid (C16:1), sapienic acid (C16:1), heptadecanoic acid (or margaric acid) (C17:0), stearic acid (C18:0), oleic acid (C18:1), arachidic acid (C20:0), eicosenoic acid (C20:1). Preferably, the fatty acid is oleic acid.

The polymerization is advantageously a free-radical polymerization conducted in the presence of a free-radical initiator, in particular a peroxide or azo type initiator.

According to a preferred embodiment of the invention, the polymerization is conducted in the presence of one or more free-radical initiators, in particular those having formula (A) or (B):

and their optical, geometric isomers and the acid salts thereof;

Formulas (A) or (B) in which:

$R_a$, $R^1$, $R^2$, $R^3$, and $R^4$, the same or different, represent a hydrogen atom or a linear or branched ($C_1$-$C_8$)alkyl group; $C_6$-$C_{10}$ aryl such as phenyl; or else $R^1$ and $R^2$ and/or $R^3$ and $R^4$ form together with the carbon atoms that bear them a 3- to 7-membered (hetero)cycloalkyl, particularly ($C_3$-$C_6$)cycloalkyl such as cyclohexyl; preferably $R_a$, $R^1$, $R^2$, $R^3$, and $R^4$, the same or different, represent a hydrogen atom or a linear or branched ($C_1$-$C_6$)alkyl group;

x and y, the same or different, represent an integer comprised between 0 and 6 inclusive, preferably x and y=0;

EA and EA, the same or different, preferably the same, represent an electron-attracting group, preferably electron-attracting through the mesomeric effect -M, such as cyano, —C($X^1$)—$X^2$—$R_a$, phosph(on)ate, sulf(on)ate, nitro, or nitroso; more particularly EA=EA'=CN;

R, and R' the same or different, preferably the same, represent i) an EA or EA' radical as defined previously, or a group chosen from ii) linear or branched ($C_1$-$C_5$) alkyl, iii) $C_6$-$C_{10}$ aryl, iv) ($C_6$-$C_{10}$)aryl($C_1$-$C_8$)alkyl, or else R with $R^1$ and/or R' with $R^3$ form together with the carbon atom that bears them a C($X^1$) group and $R^2$ and $R^4$ being as defined previously or $R^2$ and $R^4$, the same or different, represent a $R^5$—$X^2$— group in which $R^5$ represents a hydrogen atom, a linear or branched ($C_1$-$C_8$)alkyl group, a ($C_6$-$C_{10}$)aryl group such as phenyl;

X, represent a heteroatom chosen from oxygen and sulfur; preferably X represents an oxygen atom;

$X^1$, and $X^2$, the same or different, representing a heteroatom chosen from oxygen, sulfur and amino N(R") with R" being a hydrogen atom or a linear or branched ($C_1$-$C_6$)alkyl group; preferably $X^1$ and $X^2$ represent an oxygen atom.

More particularly the initiator or initiators have formula (A).

According to a specific embodiment of the invention the free-radical polymerization initiator is azo-bisisobutyronitrile (or AIBN).

According to another specific embodiment of the invention the free-radical polymerization initiator is the 2,2'-azobis-(2,4-dimethylvaleronitrile) (or ABDV or VAZO).

According to another specific embodiment of the invention the free-radical polymerization initiator is bis(4-tert-butylcyclohexyl)peroxydicarbonate.

Preferably the polymerization is conducted at a temperature comprised between 0° C. and 80° C., more particularly between 25° C. and 70° C.

The polymerization may also be conducted using ultrasound.

The polymerization may be conducted under an inert atmosphere such as argon or nitrogen.

The process for preparing the imprinted polymer according to the invention comprises:

a first polymerization step of a mixture comprising:
i) a basic ethylene monomer having an amine group as previously;
ii) one or more crosslinking agents comprising at least 2 polymerizable ethylene unsaturations;
iii) one or more porogenic solvents;
iv) one or more $C_{14}$-$C_{20}$ fatty acid(s),
v) optionally a free-radical initiator as defined previously, followed by a second step of removing the $C_{14}$-$C_{20}$ fatty acid present in the polymer obtained from the first step.

The removal step is conducted by washing the polymer obtained at the first step with a washing solvent.

The washing solvent may be chosen from $C_1$-$C_4$ alcohols, water, acetonitrile, tetrahydrofuran (THF), dialkylformamide (dimethylformamide, diethylformamide), N-methyl-2-pyrrolidinone (NMP), N-ethyl-2-pyrrolidinone (NEP), N,N'-dimethylpropylene-urea (DMPU), dimethylsulfoxide (DMSO), chloroform, acetic acid, ammonia, diethylamine, and mixtures thereof.

After the washing, the imprinted polymer no longer contains the $C_{14}$-$C_{20}$ fatty acid.

Therefore, the empty imprints allow the polymer to be able to capture oleic acid when it is applied to the scalp.

The molecularly imprinted polymer is characterized by showing that imprints have formed and assessing how many there are and how high their affinity is for the target molecule. These results can be completed by studying the material's morphology (particle size, shape, porosity and specific surface area). These methods are known by the person skilled in the art (see for example point 1.7 p. 49 in the doctoral thesis of June 2010 by R. Walsh "*Development and characterization of MIP*". http://repositorv.wit.ie/1619/1/Development and characterisation of molecularly imprinted suspension polvmers.pdf )

The cosmetic composition according to the invention is a composition that is found in a physiologically acceptable medium, which is preferably a dermatologically acceptable medium, i.e. without odour or unpleasant appearance, and which is completely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

A physiologically acceptable medium is preferably a cosmetically or dermatologically acceptable medium, that is to say a medium which is without odour or unpleasant appearance, and which is entirely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

The cosmetic composition according to the invention can be water or a mixture of water and one or more organic solvents or a mixture of organic solvents.

"Organic solvent" is understood to mean an organic substance that can dissolve or disperse another substance without changing it chemically.

The molecularly imprinted polymer according to the invention may be present in the cosmetic composition in a content ranging from 0.1% to 20% by weight, preferably ranging from 0.1% to 10% by weight and preferentially ranging from 0.1% to 5% by weight, relative to the total weight of the composition.

The composition according to the invention may comprise an additional antidandruff active agent, in particular chosen from ellagic acid and ethers thereof, ellagic acid salts and ethers thereof, pyrithione salts, 1-hydroxy-2-pyridone derivatives and selenium (poly)sulfides, and also mixtures thereof.

Ellagic acid, or 2,3,7,8-tetrahydroxy-1-benzopyrano[5,4,3-cde]-1-benzopyran-5,10-dione, is a well-known molecule that is present in the plant kingdom. Reference may be made to the published Merck Index, 20th edition (1996), No. 3588.

Ellagic acid has the following chemical formula:

which comprises four fused rings.

The ellagic acid ether(s) that may be used according to the invention are preferably chosen from the mono-, di-, tri- or polyethers obtained by etherification of one or more hydroxyl groups (one of the four OH groups of ellagic acid) of ellagic acid to one or more OR groups, R being selected from $C_2$-$C_{20}$ alkyl groups, polyoxyalkylene groups, and particularly polyoxyethylene and/or polyoxypropylene groups, and groups derived from one or more mono- or polysaccharides, for instance the group having the following formula:

In the case of the di-, tri- or polyethers of ellagic acid, the R groups as defined above may be the same or different.

Preferably, these ethers of ellagic acid are chosen from 3,4-di-O-methyl ellagic acid, 3,3'-4-tri-O-methyl ellagic acid and 3,3'-di-O-methyl ellagic acid.

The salt(s) of ellagic acid and/or of its ethers that may be used according to the invention are preferably chosen from alkali metal or alkaline-earth metal salts, such as the sodium, potassium, calcium and magnesium salt, the ammonium salt and the salts of amines such as triethanolamine, monoethanolamine, arginine and lysine salts. Preferably, the salt(s) of ellagic acid and/or of its ethers that can be used according to the invention are chosen from alkali metal or alkaline-earth metal salts, in particular the sodium, potassium, calcium or magnesium salts.

Pyrithione is the compound 1-hydroxy-2(1H)-pyridinethione or 2-pyridinethiol 1-oxide. The pyrithione salts that can be used in the scope of the invention are, in particular, monovalent metal salts and divalent metal salts, such as the sodium, calcium, magnesium, barium, strontium, zinc, cadmium, tin and zirconium salts. The divalent metal salts and particularly the zinc salt (zinc pyrithione) are particularly preferred.

The 1-hydroxy-2-pyridone derivatives are preferably chosen from compounds of formula (A1) or salts thereof:

(A1)

in which:
- R1 denotes a hydrogen atom; a linear or branched alkyl group having from 1 to 17 carbon atoms; a cycloalkyl group having 5 to 8 carbon atoms; a cycloalkyl-alkyl group, the cycloalkyl group having 5 to 8 carbon atoms and the alkyl group having from 1 to 4 carbon atoms; an aryl or aralkyl group, the aryl group having from 6 to 30 carbon atoms and the alkyl group having from 1 to 4 carbon atoms; an aryl-alkenyl group, the aryl group having from 6 to 30 carbon atoms and the alkenyl group having from 2 to 4 carbon atoms; the cycloalkyl and aryl groups as defined above may be substituted by one or more alkyl groups having 1 to 4 carbon atoms or else one or more alkoxy groups having from 1 to 4 carbon atoms;
- R2 denotes a hydrogen atom; an alkyl group having from 1 to 4 carbon atoms; an alkenyl group having from 2 to 4 carbon atoms; a halogen atom or a benzyl group;
- R3 denotes a hydrogen atom, an alkyl group having from 1 to 4 carbon atoms or a phenyl group; and
- R4 denotes a hydrogen atom; an alkyl group having from 1 to 4 carbon atoms; an alkenyl group having from 2 to 4 carbon atoms; a methoxymethyl group; a halogen atom or a benzyl group.

Among these compounds, those which are particularly preferred are constituted of 1-hydroxy-4-methyl-6-(2,4,4-trimethylpentyl)-2-(1H)-pyridone and 6-cyclohexyl-1-hydroxy-4-methyl-2-(1H)-pyridone.

The salts which can be used include the salts of lower ($C_1$-$C_4$) alkanolamines, such as ethanolamine and diethanolamine, amine or alkylamine salts, and also salts with mineral cations, for instance ammonium salts and the salts of alkali metals or alkaline-earth metals.

Very particular preference is given to the monoethanolamine salt of 1-hydroxy-4-methyl-6-(2,4,4-trimethylpentyl)-2(1H)-pyridinone (or piroctone), more commonly referred to as piroctone olamine or octopirox.

Among the selenium (poly)sulfides, mention may be made of selenium disulfide and the selenium polysulfides of formula $Se_xS_y$, in which x and y are numbers such that x+y=8. Selenium disulfide is in the form of a powder whose particles generally have a particle size of less than 200 μm and preferably less than 25 μm.

Preferably, the antidandruff agent is chosen from ellagic acid, zinc pyrithione, piroctone olamine and selenium disulfide, and also a mixture thereof.

The additional antidandruff active agents can be present in the composition according to the invention in a proportion of from 0.001% to 30% by weight and preferably in a proportion of from 0.5% to 25% by weight, with respect to the total weight of the composition.

The cosmetic composition according to the invention contains a physiologically acceptable medium.

The term "physiologically acceptable medium" means a medium that is compatible with cutaneous tissues such as the skin and the scalp.

The composition according to the invention can be provided in any formulation form conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semi-liquid consistency of the milk type, obtained by dispersion of a fatty phase in an aqueous phase (O/W) or vice versa (W/O), or of suspensions or emulsions with a soft, semi-solid or solid consistency of the cream or gel type, or alternatively of multiple emulsions (W/O/W or O/W/O), of microemulsions, of vesicular dispersions of ionic and/or non-ionic type, or of wax/aqueous phase dispersions. These compositions are prepared according to the usual methods.

The physiologically acceptable medium of the composition may more particularly consist of water and optionally of a physiologically acceptable organic solvent chosen, for example, from lower alcohols comprising from 2 to 8 carbon atoms and in particular from 2 to 6 carbon atoms, for instance ethanol, isopropanol, propanol or butanol; polyethylene glycols containing from 6 to 80 ethylene oxide units, and polyols, for instance ethylene glycol, propylene glycol, isoprene glycol, butylene glycol, glycerol and sorbitol.

The compositions according to the invention may be provided in all the formulation forms conventionally used for a topical application and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or non-ionic type (liposomes, niosomes or oleosomes). These compositions are prepared according to the usual methods.

In addition, the compositions used according to the invention may have varying degrees of fluidity and may have the appearance of a white or coloured cream, an ointment, a milk, a lotion, a serum, a paste, a mousse or a shampoo.

The composition used according to the invention comprises adjuvants commonly used in cosmetics, and chosen especially from water; oils; waxes, pigments, fillers, dyes, surfactants, emulsifiers; cosmetic active agents, UV-screening agents, polymers, thickeners, film-forming polymers, preservatives, fragrances, bactericides, odour absorbers, and antioxidants.

The amounts of these various adjuvants are those conventionally used in the field under consideration, for example from 0.01% to 20% of the total weight of the composition.

The examples that follow illustrate the invention without, however, limiting its scope.

EXAMPLE 1 (OF THE INVENTION) AND EXAMPLE 2 (OUTSIDE THE SCOPE OF THE INVENTION)

Reagents and Solvents Used

|  | Template (Oleic acid) | AB | HDM | Vazo | Methanol (anhydrous) |
|---|---|---|---|---|---|
| Example 1 MIP (invention) | 28.2 mg | 9.5 mg | 255.6 µL | 5.3 mg | 5 mL |
| Example 2 NIP (outside the scope of the invention) | 28.2 mg | 9.5 mg | 255.6 µL | 5.3 mg | 5 mL |

AB=N-acryloyl-p-aminobenzamidine; HDM=1,6-hexanediol dimethacrylate; Vazo=2,2'-azobis(2,4-dimethylvaleronitrile)

All the reagents and solvents were added to one glass flask, which was then hermetically sealed using a septum. The mixture was degassed with nitrogen for 5 min, then placed in a water bath at 40° C. for one night. After polymerization and obtaining the polymer impregnated with oleic acid (apart from that of example 2 which is not impregnated), the impregnated polymer was washed three times with 10 mL of the methanol/acetic acid mixture (9/1 vol/vol), twice with 10 mL of the NH₃ mixture (100 mM)/MeOH (7/3 vol/vol), once with 10 mL of water then twice with 10 mL of methanol. Next the imprinted polymer, thereby emptied of oleic acid, was dried under vacuum for one night. This yielded a polymer with an oleic acid imprint (MIP ex 1) and a polymer without an imprint (NIP ex 2) in the form of opaque, white, spherical particles.

EXAMPLES 3, 5, 6 (OF THE INVENTION) AND 4 (OUTSIDE THE SCOPE OF THE INVENTION)

Reagents and Solvents Used

|  | Template Oleic acid | AEM | Vpy | Hexyl methacrylate | HDM | Vazo | ACN |
|---|---|---|---|---|---|---|---|
| Example 3 (invention) | 25.2 mg | 16.56 mg | 0 | 79 µL | 0.51 mL | 10.6 mg | 10 mL |
| Example 4 (outside the scope of the invention) | 0 | 16.56 mg | 0 | 79 µL | 0.51 mL | 10.6 mg | 10 mL |
| Example 5 (invention) | 56.4 mg | 132.4 mg | 0 | 0 | 1.02 mL | 10.6 mg | 10 mL |
| Example 6 (invention) | 56.4 mg | 0 | 86 µL | 0 | 1.02 mL | 10.6 mg | 10 mL |

AEM: 2-aminoethyl methacrylate; Vpy: 4-vinylpyridine; HDM: 1,6-hexanediol dimethacrylate; ACN: acetonitrile All the reagents and solvents were added to one glass flask, which was then hermetically sealed using a septum. The mixture was degassed with nitrogen for 5 min, then placed in a water bath at 40° C. for one night. After polymerization and obtaining of the polymer impregnated with oleic acid (apart from that of example 4, which is not impregnated), the impregnated polymer was washed twice with 10 mL of a methanol/acetic acid mixture (9/1 vol/vol), twice with 10 mL of a acetonitrile/acetic acid mixture (9/1 vol/vol), once with 10 mL of acetonitrile then twice with 10 mL of methanol. Next the imprinted polymer, thereby emptied of oleic acid, was dried under vacuum for one night. This yielded a polymer with an oleic acid imprint (MIP ex 3, 5, 6) and a polymer without an imprint (NIP ex 4) in the form of opaque, white, spherical particles.

EXAMPLES 7 AND 8

Reagents and Solvents Used

|  | Template (Oleic acid) | AEM | Hexyl methacrylate | HDM | Vazo | Perkadox 16 | Pure water |
|---|---|---|---|---|---|---|---|
| Example 7 (invention) | 28.2 mg | 16.56 mg | 79 µL | 0.51 mL | 10.6 mg | 0 | 10 mL |
| Example 8 (invention) | 28.2 mg | 16.56 mg | 79 µL | 0.51 mL | 0 | 17.9 mg | 10 mL |

Perkadox 16: Bis(4-tert-butylcyclohexyl)peroxydicarbonate

Pure water was deoxygenated by bubbling nitrogen for 30 minutes. All the reagents and the solvent were added to one glass flask, which was then hermetically sealed using a septum. The mixture was degassed with nitrogen for 5 min, then placed in a sonication bath for five hours. After polymerization, the polymers were washed three times with 10 mL of a mixture of methanol/acetic acid (9/1 vol/vol), once with 10 mL of water then twice with 10 mL of methanol. Next the imprinted polymer, thereby emptied of oleic acid, was dried under vacuum for one night. This yielded a polymer with an oleic acid imprint (MIP ex 7, 8) in the form of opaque, white, spherical particles.

EXAMPLE 9

Reagents and Solvents Used

|  | Template (Oleic acid) | AB | HDM | Vazo | Dimethyl sulfoxide |
|---|---|---|---|---|---|
| Example 9 (invention) | 28.2 mg | 9.5 mg | 255.6 μL | 5.3 mg | 5 mL |

All the reagents and the solvent were added to one glass flask, which was then hermetically sealed using a septum. The mixture was degassed with nitrogen for 5 min, then placed in a water bath at 40° C. for one night. After polymerization and obtaining of the polymer impregnated with oleic acid, the impregnated polymer was washed three times with 10 mL of a methanol/acetic acid mixture (9/1 vol/vol), twice with 10 mL of an $NH_3$ (100 mM)/MeOH (7/3 vol/vol) mixture, once with 10 mL of water then twice with 10 mL of methanol. Next the imprinted polymer, thereby emptied of oleic acid, was dried under vacuum for one night. This yielded a polymer with an oleic acid imprint in the form of opaque, white, spherical particles.

EXAMPLE 10

Recognition Test (Ability of the Imprinted Polymer to Capture Oleic Acid)

The polymers with an oleic acid imprint (MIP) and the polymers without an imprint (NIP) obtained in the examples described previously were suspended in a 5/55/40 propylene glycol/ethanol/water solution (by volume) according to increasing polymer concentrations. Increasing polymer concentrations were added to 2-mL polypropylene tubes, and [3H] oleic acid (0.45 nM, 15 nano Curies) was added. The final volume was adjusted to 1 mL. The tubes were incubated for one night at room temperature on a rotating stirrer. They were then centrifuged at 16000 g for 15 min and one 500 μL aliquot of supernatant was taken and transferred to a scintillation flask containing 3 mL of scintillation liquid (reference 327123 from Fluka). The quantity of free radioligand was assayed by a scintillation counter (Beckman LS-6000 IC). This quantity was compared to that of the [3H] oleic acid solution before it was put into contact with the polymers. From the difference, the quantity of [3H] oleic acid adsorbed can be assessed.

The Following Results were Obtained:
Molecularly Imprinted Polymer (MIP) from Example 1 (of the Invention) and Polymer without an Imprint (NIP) from Example 2 (Outside the Scope of the Invention)

Figure 1:
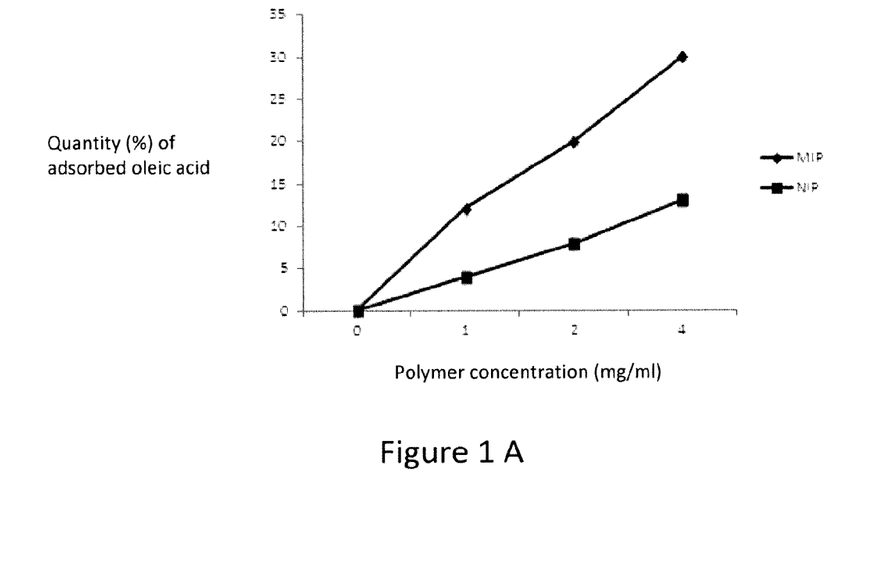
FIG. 1A is a plot of the variation of the quantity of oleic acid adsorbed as a function of the concentration of polymer.
FIG. 1B is a plot of the change in the quantity of oleic acid adsorbed as a function of the concentration of polymer.

FIG. 1A below shows the variation of the quantity of oleic acid adsorbed as a function of the concentration of polymer (MIP from example 1; NIP from example 2)

The results obtained show that the imprinted polymer (MIP) from example 1 (of the invention) can better recognize oleic acid (higher quantity of oleic acid adsorbed) than the non-imprinted polymer (NIP) from example 2 (outside the scope of the invention).

MIP from Example 3 (of the Invention) and NIP from Example 4 (Outside the Scope of the Invention):

FIG. 1B below shows the change in the quantity of oleic acid adsorbed as a function of the concentration of polymer (MIP from example 3; NIP from example 4)

The results obtained show that the imprinted polymer (MIP) from example 3 (of the invention) can better recognize oleic acid (higher quantity of oleic acid adsorbed) than the non-imprinted polymer (NIP) from example 4 (outside the scope of the invention).

EXAMPLE 11

Antidandruff Shampoo

An Anti-Dandruff Shampoo Comprising the Following Ingredients is Prepared:

| | |
|---|---|
| Sodium lauryl ether sulfate (2.2 OE) as an aqueous solution (Texapon AOS 225 UP from Cognis) | 17 g AM |
| Cocoylbetaine as an aqueous solution (Dehyton AB 30 from Cognis) | 2.5 g AM |
| Coconut acid monoisopropanolamide (Rewomid V 3203 from Goldschmidt) | 2.0 g |
| Molecularly imprinted polymer from example 1 | 1 g AM |
| Preservatives | 1.1 g |
| Fragrance | 0.5 |
| Water | qs 100 g |

When applied to the hair and scalp, the shampoo can reduce the appearance of dandruff. A similar composition is prepared with the polymers from examples 6 or 9.

EXAMPLE 12

Antidandruff Lotion

An Anti-Dandruff Lotion Comprising the Following Ingredients is Prepared:

| | |
|---|---|
| Molecularly imprinted polymer from example 3 | 5 g MA |
| Preservatives qs | |
| Water | qs 100 g |

When applied to the hair and scalp, the lotion can reduce the appearance of dandruff. A similar composition is prepared with the polymers from examples 5, 7, or 8.

The invention claimed is:
1. A cosmetic composition comprising an empty molecularly imprinted polymer prepared by:
  performing a polymerization of a pre-polymerization mixture comprising:
    i) at least one basic ethylene monomer comprising at least one amine group;
    ii) at least one crosslinking agent comprising at least two polymerizable ethylene unsaturations;
    iii) at least one porogenic solvent; and
    iv) at least one $C_{14}$-$C_{20}$ fatty acid, and
  removing the $C_{14}$-$C_{20}$ fatty acid present in the polymer obtained from the polymerization to form a polymer comprising empty imprints; and
  adding the polymer comprising empty imprints to a physiologically acceptable medium,
  wherein the cosmetic composition comprising an empty molecularly imprinted polymer is a final product suitable for topical application to the skin and/or scalp.
2. A process for preparing a cosmetic composition comprising an empty molecularly imprinted polymer comprising:
  performing a polymerization of a pre-polymerization mixture comprising:

i) at least one basic ethylene monomer comprising at least one amine group;
ii) at least one crosslinking agent comprising at least two polymerizable ethylene unsaturations;
iii) at least one porogenic solvent; and
iv) at least one $C_{14}$-$C_{20}$ fatty acid, and removing the $C_{14}$-$C_{20}$ fatty acid present in the polymer obtained from the polymerization to form a polymer comprising empty imprints; and adding the polymer comprising empty imprints to a physiologically acceptable medium, wherein the cosmetic composition comprising an empty molecularly imprinted polymer is a final product suitable for topical application to the skin and/or scalp.

3. The process according to claim 2, wherein the at least one basic ethylene monomer comprising at least one amine group is chosen from:

acrylates, methacrylates, acrylamides, and methacrylamides having an amine group represented by formula (I):

(I)

wherein:
$R_1$ is chosen from H or methyl,
X is chosen from O or NH,
R represents a divalent $C_1$-$C_4$ alkylene group, and
Z is chosen from an —$NR_2R_3$ or —$N+R_2R_3R_4X^-$ group, wherein:
$R_2$, $R_3$, and $R_4$, independently of each other, are chosen from H or a $C_1$-$C_4$ alkyl, and $X^-$ is an anion chosen from halides, ($C_2$-$C_6$)alkyl sulfates, phosphates, ($C_2$-$C_6$)alkyl- or ($C_2$-$C_6$)alkyl ($C_6$-$C_{10}$)aryl sulfonates, acetate anions, or lactate anions;

N-(meth)acryloyl-p-aminobenzamidine represented by formula (II):

(II)

wherein:
$R'_1$ is chosen from H or methyl, and
$R'_2$, $R'_3$, and $R'_4$, independently of each other, are chosen from H or a $C_1$-$C_4$ alkyl group;

styryl amidines represented by formula (III):

(III)

wherein:
$R_5$, $R_6$, and $R_7$, independently of each other, are chosen from H or a $C_1$-$C_4$ alkyl group;

amino styrenes represented by formula (IV):

(IV)

wherein:
Z' is chosen from an —$NR_8R_9$ or —$N+R_8R_9R_{10}X^-$ group wherein: $R_8$, $R_9$ and $R_{10}$, independently of each other, are chosen from H or a $C_1$-$C_4$ alkyl; and
$X^{31}$ is an anion chosen from halides or ($C_2$-$C_6$)alkyl sulfates, phosphates, ($C_2$-$C_6$)alkyl- or ($C_2$-$C_6$)alkyl ($C_6$-$C_{10}$)aryl sulfonates, acetate anions, or lactate anions;
W is chosen from a R" or OR" group, wherein R" represents a $C_1$-$C_4$ alkyl group;
and
n is an integer equal to 0, 1 or 2; or
vinylpyridines represented by formula (V):

(V)

wherein:
Y is chosen from a R''' or OR''' group, wherein R''' represents a $C_1$-$C_4$ alkyl group; and
m is an integer equal to 0, 1 or 2.

4. The process according to claim 2, wherein the at least one basic ethylene monomer having at least one amine group is chosen from N-acryloyl-p-aminobenzamidine or 2-aminoethyl methacrylate.

5. The process according to claim 2, wherein the prepolymerization mixture further comprises at least one neutral additional ethylene monomer chosen from acrylamide, methacrylamide, $C_1$-$C_6$ alkyl acrylates, $C_1$-$C_6$ alkyl methacrylates, $C_1$-$C_6$ hydroxyalkyl acrylates, $C_1$-$C_6$ hydroxyalkyl methacrylates, acrylonitrile, styrene, ($C_1$-$C_4$)alkylstyrenes, 1-allyl-urea, 1-allyl-thiourea, or vinylpyrrolidone.

6. The process according to claim 2, wherein the at least one crosslinking agent comprising at least two polymerizable ethylene unsaturations is chosen from monomers represented by the following formulae (C3) or (C4):

(C3)

(C4)

wherein:

A represents a phenyl optionally substituted by —COOH;

$R^8$, which are the same or different, is chosen from a hydrogen atom, a linear or branched ($C_1$-$C_8$)alkyl group, a linear or branched ($C_1$-$C_6$)alkyl group, or methyl;

$X^1$ and $X^2$, which are the same or different, are chosen from a heteroatom chosen from oxygen, sulfur, or amino N(R") with R" chosen from a hydrogen atom or a linear or branched ($C_1$-$C_6$)alkyl group;

W is chosen from i) a 5- or 6-membered heteroaryl group, pyridinyl, a 5- to 8-membered heterocycloalkyl group comprising at least one oxygen atom, tetrahydrofuryl, piperazynyl, or hexahydrofuro[3,2-b]furanyl, ii) a *-A-$(CR^9R^{10})_x$-A* group wherein w is an integer equal to 2, A represents a phenyl optionally substituted by —COOH;, $R^9$ and $R^{10}$, which are the same or different, are chosen from a hydrogen atom, a ($C_1$-$C_6$)alkyl group, or methyl, x is an integer ranging from 0 to 10, and * is the attachment point to the —$X^1$—C($X^2$)—C(=$CH_2$)—$R^8$ groups; or iii) a linear or branched, saturated or unsaturated, polyvalent hydrocarbon-based chain, comprising from 1 to 20 carbon atoms optionally substituted by a hydroxy group or by a phenyl group;

n is an integer ranging from 0 to 5; and u and w, which are the same or different, are an integer ranging from 2 to 10.

7. The process according to claim 2, wherein the at least one crosslinking agent comprisSing at least two polymerizable ethylene unsaturations is chosen from monomers represented by the following formulae (C3) or (C4):

(C3)

$$W {-\!\!\left[\!X^1 \overset{\displaystyle \|}{\underset{X^2}{\overset{}{C}}} \overset{R^8}{\underset{}{\phantom{|}}}\!\right]\!}_w$$
(C4)

wherein:

A represents a phenyl optionally substituted by —COOH;

$R^8$, which are the same or different, is chosen from a linear or branched ($C_1$-$C_6$)alkyl group, or methyl;

$X^1$ and $X^2$, wherein $X^1$ is chosen from O or NH, and $X^2$ represents O; $X^1$ and $X^2$ each represent an oxygen atom, or $X^1$ forms a bond;

W is chosen from i) a 5- or 6-membered heteroaryl group, pyridinyl, a 5- to 8-membered heterocycloalkyl group comprising at least one oxygen atom, tetrahydrofuryl, piperazynyl, or hexahydrofuro[3,2-b]furanyl, ii) a *-A-$(CR^9R^{10})_x$-A* group wherein w is an integer equal to 2, A represents a phenyl optionally substituted by —COOH, $R^9$ and $R^{10}$, which are the same or different, are chosen from a hydrogen atom, a ($C_1$-$C_6$)alkyl group, or methyl, x is an integer ranging from 0 to 10, and * is the attachment point to the —$X^1$—C($X^2$)—C(=$CH_2$)—$R^8$ groups; or iii) a linear or branched, saturated or unsaturated, divalent or trivalent hydrocarbon-based chain, comprising from 1 to 20 carbon atoms optionally substituted by a hydroxy group or by a phenyl group;

n is 0 or 1; and u is 2 and w is 2 or 3.

8. The process according to claim 2, wherein the at least one crosslinking agent comprising at least two polymerizable ethylene unsaturations is chosen from:

| Name | Structure |
|---|---|
| Styrene/divinyl benzene | |
| Diisopropyl benzene | |
| 1,3-phenylene diacrylamide; 1,4-phenylene diacrylamide | |
| N,N'-1,3-phenylenebis(2-methyl-2-propenamide); N,N'-1,4-phenylenebis(2-methyl-2-propenamide) | |

-continued

| Name | Structure |
|---|---|
| 3,5-bisacrylamido-benzoic acid where R″ are identical and equal to H; and 3,5-bismethylacrylamido-benzoic acid where R″ are identical and equal to CH₃ | <br>R″ = H or CH₃ |
| 2,6-bisacryloylamidopyridine where R″ are identical and equal to H; 2,6-bismethylacryloylamidopyridine where R″ are identical and equal to CH₃ | <br>R″ = H or CH₃ |
| 1,4-diacryloylpiperazine where R″ are identical and equal to H; 1,4-dimethylacryloylpiperazine where R″ are identical and equal to CH₃ | <br>R″ = H or CH₃ |
| Ethylene glycol dimethacrylate where R″ are identical and equal to CH₃ (EGDMA); Diacrylate ethylene glycol where R″ are identical and equal to H | <br>R″ = H or CH₃ |
| Tetramethylene dimethacrylate where R″ are identical and equal to CH₃; Tetramethylene diacrylate where R″ are identical and equal to H | <br>R″ = H or CH₃ |
| Hexamethylene dimethacrylate where R″ are identical and equal to CH₃ and Hexamethylene diacrylate where R″ are identical and equal to H | <br>R″ = H or CH₃ |
| Anhydroerythritoldimethacrylate where R″ are identical and equal to CH₃ and Anhydroerythritoldiacrylate where R″ are identical and equal to H | <br>R″ = H or CH₃ |

-continued

| Name | Structure |
|---|---|
| 1,4;3,6-dianhydro-p-sorbitol-2,5-dimethacrylate where R″ are identical and equal to CH$_3$; 1,4;3,6-dianhydro-p-sorbitol-2,5-diacrylate where R″ are identical and equal to H | R″ = H or CH$_3$ |
| Isopropylenebis(1,4-phenylene)-dimethacrylate where R″ are identical and equal to CH$_3$; Isopropylenebis(1,4-phenylene)-diacrylate R″ are identical and equal to H | R″ = H or CH$_3$ |
| 2,2-bis(Hydroxymethyl)butanol trimethacrylate where R″ are identical and equal to CH$_3$ (TRIM); 2,2-bis(Hydroxymethyl)butanol triacrylate R″ are identical and equal to H | R″ = H or CH$_3$ |
| Pentaerythritol triacrylate where R″ are identical and equal to H; Pentaerythritol trimethacrylate where R″ are identical and equal to CH$_3$ | R″ = H or CH$_3$ |
| Pentaerythritol tetraacrylate where R″ are identical and equal to H (PETRA); Pentaerythritol tetramethacrylate where R″ are identical and equal to CH$_3$ | R″ = H or CH$_3$ |
| N,O-bismethacryloyl-ethanolamine where R$_c$ is equal to ethylene and R″ are identical and equal to CH$_3$ | R$_c$ = (C$_1$-C$_6$)alkylene such as ethylene<br>R″ = H or CH$_3$ |

| Name | Structure |
|---|---|
| N,N'-methylene-bis-acrylamide where $R_c$ = $CH_2$ (MDAA); or N,N-1,2-ethanediylbis(2-methyl-2-propenamide) N,N'-ethylene-bis-acrylamide where $R_c$ =$CH_2$—$CH_2$; N,N'-butylene-bis-acrylamide where $R_c$ = $CH_2$—$CH_2$—$CH_2$—$CH_2$; N,N'-hexylene-bis-acrylamide where $R_c$ = $CH_2$—$CH_2$—$CH_2$—$CH_2$—$CH_2$—$CH_2$ | <br>$R_c$ = ($C_1$-$C_6$)alkylene<br>R″ = H or $CH_3$ |

9. The process according to claim 2, wherein the at least one $C_{14}$-$C_{20}$ fatty acid (T), the at least one basic ethylene monomer having an amine group and additional ethylene monomer if present (M), and the at least one crosslinking agent (CL) added to the pre-polymerization mixture are found in a T/M/CL molar ratio ranging from 1:0.4:8 to 1:8:40.

10. The process according to claim 2, wherein the at least one porogenic solvent is chosen from water, C1-C8 alcohols, acetonitrile, tetrahydrofuran, dimethylformamide, diethylformamide, N-methyl-2-pyrrolidinone, N-ethyl-2-pyrrolidinone, N,N'-dimethylpropylene-urea, dimethylsulfoxide, or mixtures thereof.

11. The process according to claim 2, wherein the at least one $C_{14}$-$C_{20}$ fatty acid is oleic acid.

12. The process according to claim 2, wherein the polymerization is a free-radical polymerization conducted in the presence of a free-radical initiator.

13. The process according to claim 2, wherein the polymerization is conducted at a temperature ranging from about 0° C. to about 80° C.

14. The process according to claim 2, wherein the polymerization is conducted at a temperature ranging from about 25° C. to about 70° C.

15. The process according to claim 2, wherein the step of removing the $C_{14}$-$C_{20}$ fatty acid present in the polymer obtained from the polymerization comprises washing the polymer with a washing solvent chosen from C1-C4 alcohols, water, acetonitrile, tetrahydrofuran (THF), dialkylformamide (dimethylformamide, diethylformamide), N-methyl-2-pyrrolidinone (NMP), N-ethyl-2-pyrrolidinone (NEP), N,N'-dimethylpropylene-urea (DMPU), dimethylsulfoxide (DMSO), chloroform, acetic acid, ammonia, diethylamine, or mixtures thereof.

16. The molecularly imprinted polymer according to claim 1, wherein the at least one C14-C20 fatty acid is oleic acid.

\* \* \* \* \*

UNITED STATES PATENT AND TRADEMARK OFFICE
CERTIFICATE OF CORRECTION

PATENT NO. : 10,772,822 B2
APPLICATION NO. : 14/655381
DATED : September 15, 2020
INVENTOR(S) : Andrew Greaves et al.

It is certified that error appears in the above-identified patent and that said Letters Patent is hereby corrected as shown below:

In the Claims

Claim 3, Column 24, Line 16, please change "X31" to -- X- --.

Claim 6, Column 25, Line 16, after "COOH" please remove the ";".

Claim 7, Column 25, Line 28, please change "comprisSing" to -- comprising --.

Signed and Sealed this
Seventh Day of June, 2022

Katherine Kelly Vidal
*Director of the United States Patent and Trademark Office*